US011344597B2

(12) United States Patent
Arnold et al.

(10) Patent No.: US 11,344,597 B2
(45) Date of Patent: May 31, 2022

(54) COMPOSITIONS FOR REDUCING OR PREVENTING DEVELOPMENT OF SYMPTOMS OF ALCOHOL CONSUMPTION

(71) Applicant: Purify Enterprises, LLC, Berlin, MD (US)

(72) Inventors: Michael B. Arnold, Berlin, MD (US); John Foley, Suffern, NY (US)

(73) Assignee: PURIFY ENTERPRISES, LLC, Berlin, MD (US)

( * ) Notice: Subject to any disclaimer, the term of this patent is extended or adjusted under 35 U.S.C. 154(b) by 0 days.

(21) Appl. No.: 16/934,851

(22) Filed: Jul. 21, 2020

(65) Prior Publication Data

US 2022/0023365 A1    Jan. 27, 2022

(51) Int. Cl.

| | |
|---|---|
| *A61K 36/33* | (2006.01) |
| *A61K 31/197* | (2006.01) |
| *A61K 36/28* | (2006.01) |
| *A61P 25/32* | (2006.01) |
| *A61K 31/198* | (2006.01) |
| *A61K 31/375* | (2006.01) |
| *A61K 31/4415* | (2006.01) |
| *A61K 31/51* | (2006.01) |
| *A61K 31/519* | (2006.01) |
| *A61K 31/525* | (2006.01) |
| *A61K 31/714* | (2006.01) |
| *A61K 33/00* | (2006.01) |
| *A61K 33/04* | (2006.01) |
| *A61K 33/30* | (2006.01) |
| *A61K 36/484* | (2006.01) |
| *A61K 38/06* | (2006.01) |

(52) U.S. Cl.
CPC .......... *A61K 36/33* (2013.01); *A61K 31/197* (2013.01); *A61K 31/198* (2013.01); *A61K 31/375* (2013.01); *A61K 31/4415* (2013.01); *A61K 31/51* (2013.01); *A61K 31/519* (2013.01); *A61K 31/525* (2013.01); *A61K 31/714* (2013.01); *A61K 33/00* (2013.01); *A61K 33/04* (2013.01); *A61K 33/30* (2013.01); *A61K 36/28* (2013.01); *A61K 36/484* (2013.01); *A61K 38/063* (2013.01); *A61P 25/32* (2018.01)

(58) Field of Classification Search
CPC .... A61K 36/33; A61K 36/484; A61K 38/063; A61K 31/198; A61K 36/28; A61K 31/197; A61P 25/32
See application file for complete search history.

(56) References Cited

U.S. PATENT DOCUMENTS

| | | | |
|---|---|---|---|
| 8,507,015 | B2 | 8/2013 | Thorsby et al. |
| 9,603,830 | B2 | 3/2017 | Powell |
| 10,357,529 | B2 | 7/2019 | Mikhail |
| 10,398,675 | B2 | 9/2019 | Powell |
| 10,478,416 | B1 | 11/2019 | Powell |
| 2012/0219581 | A1 | 8/2012 | Zabrecky |
| 2017/0326185 | A1 | 11/2017 | Smith et al. |
| 2018/0125915 | A1 | 5/2018 | Mikhail |
| 2018/0360739 | A1 | 12/2018 | Lorenz et al. |
| 2019/0343776 | A1 | 11/2019 | Kaplan et al. |
| 2020/0016117 | A1 | 1/2020 | Powell |

FOREIGN PATENT DOCUMENTS

| | | |
|---|---|---|
| BE | 1023090 B1 | 11/2016 |
| BE | 1026122 B1 | 10/2019 |
| CA | 3049326 A1 | 1/2020 |
| KR | 20090078662 A | 7/2009 |

OTHER PUBLICATIONS

Maksoud et al. Ameliorative effect of liquorice extract versus silymarin in experimentally induced chronic hepatitis: A biochemical and genetical study. Clinical Nutrition Experimental 23 (2019) 69-79. (Year: 2019).*
Epstein, "Alcohol's Impact on Kidney Function", Alcohol Health & Research World, vol. 21, No. 1, p. 84-92, Jan. 1997.
Wiese, et al., "Effect of Opuntia Ficus Indica on Symptoms of the Alcohol Hangover", Archives of Internal Medicine, Jun. 28, 2004.
Sabbadin, et al., "Licorice: From Pseudohyperaldosteronism to Therapeutic Uses" Frontiers in Endocrinology, vol. 10, Jul. 18, 2019 (available at https://www.frontiersin.org/articles/10.3389/fendo.2019.00484/full).
Subramanya, et al., "Inhibition of Intestinal Biotin Absorption by Chronic Alcohol Feeding: Cellular and Molecular Mechanisms", American Journal of Physiology Gastrointestinal and Liver Physiology, Dec. 9, 2010, 18 pages.
"The Best Milk Thistle Supplements Of 2020", Smarter Reviews, Accessed via: (https://smarter-reviews.com/lp/milk-thistle-supplements) on Jan. 21, 2021, 17 pages.
"Niacin and Alcohol / Food Interactions" Accessed via: (https://www.drugs.com/food-interactions/niacin.html) on Jan. 21, 2021, 2 pages.
Adams "Licorice Root Reduces Liver Damage from Alcohol", The Journal of Plant Medicines, Mar. 16, 2017, Accessed via: (https://plantmedicines.org/licorice-root-reduces-liver-damage-alcohol/) on Jan. 21, 2021, 8 pages.

(Continued)

*Primary Examiner* — Lakshmi S Channavajjala
(74) *Attorney, Agent, or Firm* — Dinsmore & Shohl, LLP

(57) ABSTRACT

A composition for reducing or preventing development of one or more symptoms of alcohol consumption includes at least prickly pear extract, reduced L-Glutathione, N-Acetyl-L-Cysteine (NAC), licorice root extract, and milk thistle, which are present in the composition in effective amounts sufficient in combination to reduce or prevent development of one or more detrimental symptoms of alcohol consumption. Also disclosed are methods of reducing or prevent the development of detrimental symptoms of alcohol consumption using the compositions.

18 Claims, No Drawings

(56) References Cited

OTHER PUBLICATIONS

J. Petra; My PreToxx Review: Prickly Pear & Milk Thistle a Viable Hangover Remedy; Mar. 11, 2014; 15 pgs.; Retrieved from the Internet: U RL:https://web.archive.org/web/2016032318, 5154/ https://hangovercure.org/hangover-cures/reviews/pretoxx/ [retrieved on Sep. 20, 2019].
Gastroenterology, Elsevier Inc, US; Abstracts of the AASLD; vol. 130, No. 4, Apr. 1, 2006 (Apr. 1, 2006) 1-15, pp. A-748, XP005643845, ISSN: 0016-5085, paragraph [S1584;S1603].
International Searching Authority; International Search Report and the Written Opinion of the International Searching Aughority, or the Declaration; dated Nov. 5, 2021, 236 pgs.

\* cited by examiner

COMPOSITIONS FOR REDUCING OR PREVENTING DEVELOPMENT OF SYMPTOMS OF ALCOHOL CONSUMPTION

TECHNICAL FIELD

The present disclosure relates to compositions for promoting healthy lifestyles, in particular, to compositions for reducing or preventing development of symptoms of alcohol consumption.

BACKGROUND

The consumption of alcoholic beverages, such as wine, beer, and liquor, has become an important aspect in the social and professional cultures of people in many countries around the world. In addition to alcoholic beverages, alcohol, specifically ethanol, may also be present in many foods, medicines, and other products routinely consumed by people. Alcohol from these products is absorbed into the human body through the gastrointestinal system and can have both beneficial and detrimental effects on the human body. Detrimental effects from the consumption of alcohol can include but are not limited to dehydration, fatigue, inflammation, headache, gastrointestinal discomfort, and increased heart rate, among other effects. These detrimental effects of alcohol consumption can lead to reduced productivity and a decrease in overall quality of life, particularly the day after consuming the alcohol.

SUMMARY

Therefore, ongoing needs exist for compositions and treatments for reducing or preventing the development of detrimental effects of alcohol consumption, such as hangover and lost productivity. The compositions and methods of the present disclosure meet these needs by providing a composition comprising an active blend of ingredients that can reduce or prevent development of the detrimental effects of alcohol consumption. The compositions of the present disclosure include an active blend that includes prickly pear extract, reduced L-Glutathione, N-Acetyl-L-Cysteine (NAC), licorice root extract, and milk thistle. The prickly pear extract, reduced L-Glutathione, NAC, licorice root extract, and milk thistle work synergistically in combination to reduce or prevent development of detrimental symptoms of alcohol consumption. Reduced L-Glutathione is a key component in the liver for breaking down alcohol, N-Acetyl-L-Cysteine (NAC) promotes further synthesis of L-Glutathione, the prickly pear extract provides anti-inflammatory effects, the licorice root extract may soothe stomach discomfort and regulate metabolism, and milk thistle can further promotes liver function, while all act as antioxidants and scavenge free radicals. The composition comprising the active blend may improve metabolism of alcohol, reduce inflammation, boost immune system response, promote healthy cortisol levels, and relieve stomach discomfort, among other benefits.

According to one or more aspects of the present disclosure, a composition for reducing or preventing development of one or more symptoms of alcohol consumption may include at least prickly pear extract, reduced L-Glutathione, N-Acetyl-L-Cysteine (NAC), licorice root extract, and milk thistle.

According to one or more other aspects of the present disclosure a method of preventing or reducing the development of one or more detrimental symptoms of alcohol consumption may include administering a liquid mixture to a human being before or after consuming one or more alcoholic beverages, where the liquid mixture may include water and a composition that may include effective amounts of each of prickly pear extract, reduced L-Glutathione, N-Acetyl-L-Cysteine (NAC), licorice root extract, and milk thistle in order to reduce or prevent development of one or more symptoms of alcohol consumption.

DETAILED DESCRIPTION

As previously discussed, consumption of alcoholic beverages is increasing in popularity around the world and had become an important aspect of professional and recreational life. Beverages containing alcohol, in particular ethanol, can include beer, wine and liquors. Alcohol can also be present in many foods, medicines, and other products. The ethanol from consuming these alcoholic beverages is adsorbed into the bloodstream through the gastrointestinal (GI) system and is distributed throughout the body via the bloodstream. Alcohol distributed throughout the body can affect the brain, heart, and liver, among other organs. In particular, alcohol is a depressant that can interfere with normal operation of the nervous system and induce a state of intoxication, which has been associated with changes in behavior and mood, decreases in cognitive abilities, and slowing of reflexes and motor skills, among other effects. The degree of intoxication from a fixed amount of alcohol may vary from person to person. Chronic alcohol consumption can lead to liver disease and may impact kidney function. In particular, both acute and chronic alcohol consumption can result changes in the structure and function of the kidneys and may adversely impact the ability of the kidneys to regulate fluids and electrolyte concentration in the body. Epstein, Murray, "Alcohol's Impact on Kidney Function," *Alcohol Health and Research World*, Vol. 21, No. 1 (1997).

Alcohol is eventually removed from the body by the liver, which breaks down the ethanol first into acetaldehyde and other toxic intermediates. The acetaldehyde and other toxin intermediates are further metabolized into less harmful constituents such as acetates and the like. Removing alcohol from the bloodstream can leave the liver deficient in substances, such as L-glutathione, which are critical components in the process of ridding the body of toxins. These deficiencies may temporarily reduce the body's ability to effectively remove toxins, such as lactic acid, from the bloodstream and may ultimately lead to inflammation or damage to the liver and chronic liver problems.

Once the state of intoxication subsides and the liver removes the alcohol from the bloodstream, the person may be left with a hangover, which may include any of a number of detrimental symptoms of alcohol consumption of varying degrees. These detrimental symptoms of hangover or alcohol consumption can include inflammation and other effects of acetaldehyde and other toxic intermediates, headache, dehydration, fatigue, GI discomfort, sleep disruption, decreased blood sugar, and loss of micronutrients, such as vitamins, minerals, and electrolytes, among other detrimental effects. These detrimental effects can persist for hours and even days, depending on the amount of alcohol consumed and the ability of the person to metabolize the alcohol, and the severity of these symptoms may be related to inflammation caused by the intermediates and byproducts produced during metabolism of the alcohol and/or impurities in the alcoholic beverage consumed. These detrimental effects of alcohol consumption can adversely affect quality of life and ability to work effectively, thus, lowering productivity.

Commercially available products exist for treating hangovers and include various end of the night or morning after remedies intended to treat the symptoms of hangover. However, the commercially available hangover remedies are not generally designed to proactively reduce or prevent development of these detrimental symptoms before they arise. Therefore, there is an ongoing need for compositions and methods for reducing or preventing the development of one or more detrimental effects of alcohol consumption before they arise.

The present disclosure is related to compositions and methods for improving metabolism of alcohol by human beings and proactively reducing or preventing the development of the detrimental symptoms and effects of alcohol consumption in human beings. In aspects of the present disclosure, the compositions for improving metabolism of alcohol and reducing or preventing development of detrimental effects from consumption of alcohol may include an active blend comprising prickly pear extract, reduced L-Glutathione, N-Acetyl-L-Cysteine (NAC), licorice root extract, and milk thistle. The constituents of the active blend may each be present in effective amounts that, when combined, may work synergistically in combination to reduce or prevent development of detrimental symptoms of alcohol consumption. Reduced L-Glutathione is a key component in the liver for breaking down alcohol, NAC promotes further synthesis of L-Glutathione, the prickly pear extract provides anti-inflammatory effects, the licorice root extract may soothe stomach discomfort and regulate metabolism, and milk thistle can further promotes liver function, while all act as antioxidants and scavenge free radicals. Thus, the reduced L-Glutathione, NAC, prickly pear extract, licorice root extract, and milk thistle may work synergistically to proactively boost liver function and increase antioxidant levels to combat the detrimental effects of alcohol consumption before, during, and after consumption of alcohol.

The composition may also include micronutrients, such as but not limited to Biotin and other vitamins, minerals, and electrolytes; fillers or sweeteners; flavorings; colorants; citric acid/citrates; or other additives. The present disclosure is also related to methods of using the compositions disclosed herein to improve metabolism of alcohol and/or to reduce or prevent the development of detrimental symptoms of alcohol consumption before or during consumption of alcohol. The compositions and methods of the present disclosure may proactively improve the metabolism of alcohol by the human body and may proactively reduce or prevent development of the symptoms of alcohol consumption in human beings, among other benefits.

As used herein, the term "alcohol" refers to ethanol, and the term "alcoholic beverage" may refer to a beverage containing ethanol that is intended for human consumption.

As used herein, the term "micronutrients" is used to refer to one or more of vitamins, minerals, and electrolytes.

As used herein, the terms "serving size," "dose," and "dosage," when used relative to the composition for reducing or preventing development of the symptoms of alcohol consumption, may refer to an amount required for administering one treatment of the composition. The terms "serving size," "dosage," and "dose" may be used interchangeably through the present disclosure.

As used herein, the term "extract" may refer to a composition that is extracted from a plant using known extraction techniques and that includes one or more compounds providing one or more therapeutic properties to the composition.

As previously discussed, the composition of the present disclosure for improving metabolism of alcohol and reducing or preventing development of detrimental symptoms of alcohol consumption may include an active blend comprising effective amounts of each of prickly pear extract, reduced L-Glutathione, N-Acetyl-L-Cysteine (NAC), licorice root extract, and milk thistle. The composition may further include micronutrients, such as Biotin, vitamins, minerals, electrolytes, or combinations of these. The composition may also include fillers, flavorings, colorants, or other additives.

As previously discussed, the active blend of the composition may include prickly pear extract in effective amounts. Prickly pear extract is an extract from the *Opuntia ficus indica* (OFI), which is a member of the cactus family. The prickly pear extract may be extracted from the OFI by any known extraction process. The prickly pear extract may include compounds that provide antioxidant and anti-inflammatory effects, among other potential benefits. The prickly pear extract may be included in the composition to aide in reducing inflammation, which may be caused by various byproducts and intermediates, such as acetaldehyde, lactic acid, and other toxins, produced during metabolism of alcohol in the human body. The prickly pear extract may provide other health benefits in addition to its antioxidant and anti-inflammatory effects.

The composition may include an effective amount of prickly pear extract that is an amount sufficient to provide an anti-inflammatory effect on the human body when the composition is ingested. The composition may include greater than or equal to 0.5 weight percent (wt. %), greater than or equal to 1.0 wt. %, or greater than or equal to 1.5 wt. % prickly pear extract based on the total weight of the composition. The composition may include less than or equal to 6.0 weight percent (wt. %), less than or equal to 3.0 wt. %, or less than or equal to 2.0 wt. % prickly pear extract based on the total weight of the composition. The composition may include from 0.5 wt. % to 6.0 wt. %, from 0.5 wt. % to 3.0 wt. %, from 0.5 wt. % to 2.0 wt. %, from 0.5 wt. % to 1.5 wt. %, from 1.0 wt. % to 6.0 wt. %, from 1.0 wt. % to 3.0 wt. %, from 1.0 wt. % to 2.0 wt. %, from 1.5 wt. % to 6.0 wt. %, from 1.5 wt. % to 3.0 wt. %, from 1.5 wt. % to 2.0 wt. %, from 2.0 wt. % to 6.0 wt. %, or from 2.0 wt. % to 3.0 wt. % prickly pear extract based on the total weight of the composition. A single serving size of 10 grams of the composition may include greater than or equal to 50 milligrams (mg), greater than or equal to 100 mg, or greater than or equal to 150 mg prickly pear extract. A single serving size of 10 grams of the composition may include less than or equal to 600 mg, less than or equal to 300 mg, or even less than or equal to 200 mg prickly pear extract. When the concentration of prickly pear extract is less than 50 mg in a 10 gram serving size of the composition, the amount of prickly pear extract may not be sufficient to provide effective anti-inflammatory effects.

The composition may further include L-glutathione. L-glutathione is an substance that acts as an antioxidant and is present in most cells, but may be found in greater concentrations in organs such as the liver, spleen, and heart. L-glutathione is a biologically active sulfur tripeptide and, the sulfur present in the L-glutathione may provide active sites for binding toxins. As an antioxidant, L-glutathione may react with free radicals present in cells to neutralize the free radicals, thereby reducing oxidative stress in cells. In the liver, L-glutathione can play a role in breaking down alcohol, in particular, L-glutathione may contribute to breaking down acetaldehyde and other toxins to less harmful chemicals. L-glutathione may additionally promote liver health and/or may further support the immune system, among other benefits. The L-glutathione can exist in the reduced or oxidized state, although the reduced state provides the antioxidant benefits. The ratio of oxidized glutathione to reduced glutathione may be an indicator of oxidative stress in human cells. For example, increased ratios of oxidized glutathione to reduced glutathione may indicate a state of oxidative stress. In embodiments, the composition may include reduced L-glutathione.

The composition may include an effective amount of reduced L-glutathione sufficient to provide antioxidant properties and promote metabolism of alcohol, such as converting acetaldehyde and other byproducts to less toxic species. The composition may include greater than or equal to 0.5 wt. %, greater than or equal to 1.0 wt. %, or greater than or equal to 1.5 wt. % reduced L-glutathione based on the total weight of the composition. The composition may include less than or equal to 6.0 weight percent (wt. %), less than or equal to 3.0 wt. %, or less than or equal to 2.0 wt. % reduced L-glutathione based on the total weight of the composition. The composition may include from 0.5 wt. % to 6.0 wt. %, from 0.5 wt. % to 3.0 wt. %, from 0.5 wt. % to 2.0 wt. %, from 0.5 wt. % to 1.5 wt. %, from 1.0 wt. % to 6.0 wt. %, from 1.0 wt. % to 3.0 wt. %, from 1.0 wt. % to 2.0 wt. %, from 1.0 wt. % to 1.5 wt. %, from 1.5 wt. % to 6.0 wt. %, from 1.5 wt. % to 3.0 wt. %, from 1.5 wt. % to 2.0 wt. %, from 2.0 wt. % to 6.0 wt. %, or from 2.0 wt. % to 3.0 wt. % reduced L-glutathione based on the total weight of the composition. A single serving size of 10 grams of the composition may include greater than or equal to 50 milligrams (mg), greater than or equal to 100 mg, or greater than or equal to 150 mg reduced L-glutathione. A single serving size of 10 grams of the composition may include less than or equal to 600 mg, less than or equal to 300 mg, or even less than or equal to 200 mg L-glutathione. When the concentration of reduced L-glutathione is less than 50 mg in a 10 gram serving size of the composition, the amount of reduced L-glutathione may not be sufficient to promote increased metabolism of alcohol and byproducts of alcohol metabolism. When the L-glutathione is present in amounts greater than or equal to 600 mg in a 10 gram sample of the composition, the L-glutathione may produce a slight sulfurous odor when mixed with water during preparation of a liquid mixture using the composition. For example, L-glutathione includes 3 amino acids, when oxidized with water and air (air does not affect powder form) one of the amino acids yields a slight sulfuric odor. L-glutathione may have a very tangy sour taste. L-glutathione is a biologically active sulfur tripeptide and, therefore, may have a slight sulfurous odor or smell, which may be often compared to the odor of rotten eggs. Sulfur is the reason the L-glutathione is so good at binding toxins. Maintaining the amount of L-glutathione in the composition less than or equal to 600 mg in a 10 mg sample of the composition may reduce the sulfurous odor produced by the composition when mixed with water.

The active blend of the composition may further include N-Acetyl-L-Cysteine (NAC). NAC is a natural precursor to L-Glutathione and may be included in the composition to reduce further the toxic effects of acetaldehyde and other toxic byproducts produced during the metabolism of alcohol. NAC is the acetylated variant of the amino acid L-cysteine and, in the cells, may be converted to metabolites that promote synthesis of L-glutathione. Thus, the inclusion of NAC may promote further synthesis of L-glutathione in the liver. The NAC may also be an antioxidant capable of scavenging free radicals produced during the metabolism of alcohol or otherwise. Thus, NAC may also independently promote detoxification through scavenging free radicals. NAC may also reduce or prevent development of alcohol-related liver damage.

The active blend of the composition may include an effective amount of NAC that is an amount sufficient to provide antioxidant properties and promote metabolism of alcohol, such as converting acetaldehyde and other byproducts to less toxic species. The composition may include greater than or equal to 0.5 wt. %, greater than or equal to 0.75 wt. %, or greater than or equal to 1.0 wt. % NAC based on the total weight of the composition. The composition may include less than or equal to 6.0 weight percent (wt. %), less than or equal to 3.0 wt. %, less than or equal to 2.5 wt. %, or less than or equal to 2.0 wt. % NAC based on the total weight of the composition. The composition may include from 0.5 wt. % to 6.0 wt. %, from 0.5 wt. % to 3.0 wt. %, from 0.5 wt. % to 2.5 wt. %, from 0.5 wt. % to 2.0 wt. %, from 0.75 wt. % to 6.0 wt. %, from 0.75 wt. % to 3.0 wt. %, from 0.75 wt. % to 2.5 wt. %, from 0.75 wt. % to 2.0 wt. %, from 1.0 wt. % to 6.0 wt. %, from 1.0 wt. % to 3.0 wt. %, from 1.0 wt. % to 2.5 wt. %, from 1.0 wt. % to 2.0 wt. %, or from 2.0 wt. % to 6.0 wt. % NAC based on the total weight of the composition. A single serving size of 10 grams of the composition may include greater than or equal to 50 milligrams (mg), greater than or equal to 75 mg, or greater than or equal to 100 mg NAC. A single serving size of 10 grams of the composition may include less than or equal to 600 mg, less than or equal to 300 mg, less than or equal to 250, or even less than or equal to 200 mg NAC. When the concentration of NAC is less than 50 mg in a 10 gram serving size of the composition, the amount of NAC may not be sufficient to promote increased metabolism of alcohol and byproducts of alcohol metabolism.

As previously discussed, the active blend of the composition may further include licorice rood extract. The licorice root extract may be included to soothe the stomach to relieve GI discomfort associated with alcohol consumption. In cases of food poisoning, stomach ulcers, and heartburn, licorice root extract can speed the repair of stomach lining and restore balance. This is due to the anti-inflammatory and immune-boosting properties of glycyrrhizin acid. Licorice root extract contains glycyrrhizin acid, which is not present in ginger root or other common extracts commonly used for soothing GI discomfort. The glycyrrhizin acid provides anti-inflammatory and immune-boosting properties to the composition disclosed herein.

The licorice root extract can also have an impact on the adrenal system of the human body. The adrenal gland produces cortisol and adrenaline in response to stress. Cortisol plays a large role in regulating metabolism. Cortisol stimulates the liver to increase production of blood sugar and also helps the body covert fats, proteins, and carbohydrates into usable energy. Cortisol is part of the body's "fight or flight" response and is released during stressful times to provide your body with a natural boost of energy. If cortisol levels are constantly high, such as due to chronic stress, the effects may result in insulin resistance and type 2 diabetes. Cortisol levels reach their highest in the am, peaking around 9 am, before starting to decline again throughout the day. This "normal" pattern alters when people work irregular job shifts, get too much sleep during the day, or stress the body with alcohol. Alcohol can have in effect on the amount of cortisol that is produced in the human body. In particular, continuous consumption of alcohol over an extended period can increase cortisol levels in the body. Cortisol is released during periods of high stress and can result in the temporary shutdown of other physical processes, causing physical damage to the body.

The licorice root extract in the compositions of the present disclosure can provide relief for these effects of increased cortisol release during periods of alcohol consumption. When stress leaves the adrenal gland, the adrenal gland may be exhausted from producing adrenaline and cortisol. The licorice root extract can provide relief by stimulating the adrenal gland, which can promote a healthy level of cortisol in the body. See C. Sabbadin, et al., "Licorice: From Pseudohyperaldosteronism to Therapeutic Uses," Front. Endocrinol., 18 Jul. 2019, (available at https://www.frontiersin.org/articles/10.3389/fendo.2019.00484/full), which is incorporated by references herein in its entirety. Additionally, the licorice root extract may provide a sweetening flavor to the compositions of the present disclosure. Licorice root extract may include at least 50 times the sugar of other extracts, such as ginger root extract, which may have more of a spiced flavor.

The active blend of the composition may include an effective amount of licorice root extract that is an amount sufficient to relieve stomach discomfort and/or promote healthy cortisol levels in the body. The composition may include greater than or equal to 0.5 wt. %, greater than or equal to 0.7 wt. %, or greater than or equal to 1.0 wt. % licorice root extract based on the total weight of the composition. The composition may include less than or equal to 6.0 weight percent (wt. %), less than or equal to 3.0 wt. %, or even less than or equal to 2.0 wt. % licorice root extract based on the total weight of the composition. The composition may include from 0.5 wt. % to 6.0 wt. %, from 0.5 wt. % to 3.0 wt. %, from 0.5 wt. % to 2.0 wt. %, from 0.7 wt. % to 6.0 wt. %, from 0.7 wt. % to 3.0 wt. %, from 0.7 wt. % to 2.0 wt. %, from 1.0 wt. % to 6.0 wt. %, from 1.0 wt. % to 3.0 wt. %, from 1.0 wt. % to 2.0 wt. %, or from 2.0 wt. % to 6.0 wt. % licorice root extract based on the total weight of the composition. A single serving size of 10 grams of the composition may include greater than or equal to 50 milligrams (mg), greater than or equal to 70 mg, or greater than or equal to 100 mg licorice root extract. A single serving size of 10 grams of the composition may include less than or equal to 600 mg, less than or equal to 300 mg, or even less than or equal to 200 mg licorice root extract. When the concentration of licorice root extract is less than 50 mg in a 10 gram serving size of the composition, the amount of licorice root extract may not be sufficient to promote healthy levels of cortisol in the body and/or relieve stomach discomfort.

As previously discussed, the active blend of the composition may further include milk thistle that includes silymarin, which is an active component having antioxidant properties. The milk thistle may be a milk thistle extract that includes the silymarin. The silymarin in the milk thistle extract may act as an antioxidant and may contribute to scavenging free radicals in the body and breaking down acetaldehyde and other toxins. The milk thistle may further promote liver functionality in breaking down toxic substances and to combat oxidative stress. The milk thistle may also reduce and reverse damage to the liver caused by free radicals and toxins. The milk thistle may be a milk thistle extract comprising at least 80 wt. % silymarin based on the total weight of the milk thistle extract.

The active blend of the composition may include an effective amount of milk thistle that is an amount sufficient to provide further antioxidant properties to the composition and promote liver function to breakdown acetaldehyde and other toxins produced during metabolism of alcohol. The composition may include greater than or equal to 0.2 wt. %, greater than or equal to 0.3 wt. %, greater than or equal to 0.5 wt. %, or even greater than or equal to 1.0 wt. % milk thistle or milk thistle extract based on the total weight of the composition. The composition may include less than or equal to 6.0 wt. %, less than or equal to 3.0 wt. %, less than or equal to 2.0 wt. %, or less than or equal to 1.0 wt. % milk thistle or milk thistle extract based on the total weight of the composition. The composition may include from 0.2 wt. % to 6.0 wt. %, from 0.2 wt. % to 3.0 wt. %, from 0.2 wt. % to 2.0 wt. %, from 0.2 wt. % to 1.0 wt. %, from 0.3 wt. % to 6.0 wt. %, from 0.3 wt. % to 3.0 wt. %, from 0.3 wt. % to 2.0 wt. %, from 0.3 wt. % to 1.0 wt. %, from 1.0 wt. % to 6.0 wt. %, from 1.0 wt. % to 3.0 wt. %, from 1.0 wt. % to 2.0 wt. %, or from 2.0 wt. % to 6.0 wt. % milk thistle or milk thistle extract based on the total weight of the composition. A single serving size of 10 grams of the composition may include greater than or equal to 20 milligrams (mg), greater than or equal to 30 mg, greater than or equal to 50 mg, or greater than or equal to 100 mg milk thistle or milk thistle extract. A single serving size of 10 grams of the composition may include less than or equal to 600 mg, less than or equal to 300 mg, less than or equal to 200 mg, or even less than or equal to 100 mg milk thistle or milk thistle extract. When the concentration of milk thistle or milk thistle extract is less than 20 mg in a 10 gram serving size of the composition, the amount of milk thistle extract may not be sufficient to provide further antioxidant properties to the composition and promote liver function to breakdown acetaldehyde and other toxins produced during metabolism of alcohol.

The composition may further include one or more micronutrients, such as vitamins, minerals, electrolytes, or combinations of these. The composition may include vitamins, such as but not limited to Vitamin C, Vitamin E, one or more B Vitamins, or combinations of these to replenish these vitamins, which may be lost through consumption of alcohol. In embodiments, the composition may include Vitamin C, which may promote the immune system. When present, Vitamin C may be present as ascorbic acid. The composition may include from 0.5 wt. % to 6 wt. % Vitamin C based on the total weight of the composition. A 10 gram sample of the composition may include from 1 mg to 300 mg or from 10 mg to 200 mg Vitamin C.

The composition may include one or more B vitamins such as but not limited to B-1 (thiamine), B-2 (riboflavin), B-5 (pantothenic acid), B-6, B-7 (biotin), B-9 (folate), B-12, or combinations of these. The B vitamins may be added to replace B vitamins lost through consumption and metabolism of alcohol. The B vitamins included in the composition may help to reduce or prevent development of headache caused by consumption of alcohol, among other effects. The B vitamins may be included as part of a B vitamin complex or may be added as individual constituents to the composition.

The composition may include Biotin (Vitamin B-7), which is an essential compound in the growth and development of cells. Alcohol consumption in humans can reduce adsorption of biotin into the body, thereby, reducing the levels of biotin. Biotin may be included in the composition to increase the amount of biotin adsorbed into the body to help restore biotin levels depleted through alcohol consumption. The composition may include greater than or equal to 0.001 wt. %, greater than or equal to 0.005 wt. %, greater than or equal to 0.01 wt. % Biotin based on the total weight of the composition. The composition may include less than or equal to 0.2 wt. %, less than or equal to 0.15 wt. %, or less than or equal to 0.1 wt. % Biotin based on the total weight of the composition. The composition may include from 0.001 wt. % to 0.2 wt. %, from 0.001 wt. % to 0.15 wt. %, from 0.001 wt. % to 0.1 wt. %, from 0.005 wt. % to 0.2 wt. %, from 0.005 wt. % to 0.15 wt. %, from 0.005 wt. % to 0.1 wt. %, from 0.01 wt. % to 0.2 wt. %, from 0.01 wt. % to 0.15 wt. %, from 0.01 wt. % to 0.1 wt. %, or from 0.1 wt. % to 0.2 wt. % Biotin based on the total weight of the composition. A single serving size of 10 grams of the composition may include greater than or equal to 0.1 milligrams (mg), greater than or equal to 0.5 mg, or greater than or equal to 1 mg Biotin A single serving size of 10 grams of the composition may include less than or equal to 20 mg, less than or equal to 15 mg, or even less than or equal to 10 mg Biotin.

The composition may also include one or more other B vitamins, such as but not limited to thiamine (B-1), riboflavin (B-2), pantothenic acid (B-5), B-6, folate (B-9), B-12, or combinations of these. In embodiments, the composition may include thiamine. When included in the composition, the thiamine may be included as thiamine hydrochloride. A 10 gram dosage amount of the composition may include from 0.01 mg to 1 mg thiamine hydrochloride. In embodiments, the composition may include riboflavin. A 10 gram dosage amount of the composition may include from 0.01 mg to 1 mg riboflavin. In embodiments, the composition may include Vitamin B-5. When included in the composition, the Vitamin B-5 may be included as calcium D pentothenate. A 10 gram dosage amount of the composition may include from 0.01 mg to 5 mg or from 0.1 mg to 4 mg calcium D pentothenate (vitamin B-5). In embodiments, the composition may include Vitamin B-6. When included in the composition, the Vitamin B-6 may be included as pyridoxine hydrochloride. A 10 gram dosage amount of the composition may include from 0.01 mg to 5 mg or from 0.1 mg to 5 mg pyridoxine hydrochloride (Vitamin B-6). In embodiments, the composition may include folate (Vitamin B-9). When included in the composition, the folate may be included in the form of folic acid. A 10 gram dosage amount of the composition may include from 1 microgram (mcg) to 200 mcg folic acid (Vitamin B-9). In embodiments, the composition may include vitamin B-12. When included in the composition, the Vitamin B-12 may be included as a solution of cyanocobalamin. A 10 gram dosage amount of the composition may include from 0.1 mcg to 20 mcg Vitamin B-12. It is understood that other vitamins may be included in the composition without reduction in the effectiveness of the composition.

In embodiments, the composition does not include niacin (Vitamin B-3). Niacin (Vitamin B-3) may interact with alcohol. In particular, consuming alcohol, such as ethanol, together with niacin may increase some of the side effects of niacin, such as but not limited to nausea, dizziness, itching, vomiting, upset stomach, and flushing (warmth, redness, or tingly feeling under your skin). Thus, the presence of niacin in the composition may counteract the beneficial effects of the composition of reducing or preventing development of detrimental symptoms of alcohol consumption, and may exacerbate the detrimental effects of alcohol consumption. Therefore, the compositions of the present disclosure do not include niacin.

The micronutrients included in the composition may further include one or more minerals, such as but not limited to zinc, selenium, magnesium, other minerals, or combinations of these. Zinc, selenium, or both may be included in the composition to improve the effectiveness of the milk thistle.

In embodiments, the composition may include both zinc and selenium. When included in the composition the zinc may be include as a zinc compound, such as but not limited to zinc gluconate. The composition may include greater than or equal to 0.001 wt. % or greater than or equal to 0.01 wt. % zinc based on the total weight of the composition. The composition may include less than or equal to 0.10 wt. % or less than or equal to 0.05 wt. % zinc based on the total weight of the composition. In embodiments, the 10 gram dosage amount of the composition may include 3 mg zinc. A 10 gram dosage amount of the composition may include from 0.1 mg to 10 mg, from 0.1 mg to 5 mg, from 1.0 mg to 10 mg, or from 1.0 mg to 5.0 mg zinc. In embodiments, the composition may not include zinc. When present, selenium may be included as a selenium salt, such as but not limited to sodium selenite. A 10 gram dosage amount of the composition may include from 1 mcg to 50 mcg, from 1 mcg to 30 mg, from 1 mcg to 20 mcg, from 5 mcg to 50 mcg, from 5 mcg to 30 mcg, or from 5 mcg to 20 mcg selenium. In embodiments, a 10 gram dosage amount of the composition may include 11 mcg selenium. In embodiments, the composition may not include magnesium.

The micronutrients included in the composition may further include one or more electrolytes, Electrolytes may be included in the composition to replace electrolytes lost during the consumption of alcohol. The electrolytes may reduce or prevent the effects of dehydration and headaches that may result from consumption of alcohol. Electrolytes may include, but are not limited to sodium, potassium, chloride, calcium, magnesium, bicarbonate, phosphate, sulfate, salts thereof, or combinations of these. In embodiments, electrolytes may include one or more of calcium, sodium, potassium, bicarbonates, phosphate, combinations of these, or salts thereof. In embodiments, the composition may include potassium bicarbonate, sodium bicarbonate, calcium triphosphate, or combinations of these. The composition may include greater than or equal to 0.1 wt. %, greater than or equal to 1 wt. %, or greater than or equal to 5 wt. % electrolytes based on the total weight of the composition. The composition may include less than or equal to 15 wt. %, less than or equal to 10 wt. %, or even less than or equal to 8 wt. % electrolytes based on the total weight of the composition. In embodiments, the composition may include from 0.1 wt. % to 15 wt. %, from 0.1 wt. % to 10 wt. %, from 0.1 wt. % to 8 wt. %, from 1.0 wt. % to 15 wt. %, from 1.0 wt. % to 10 wt. %, from 1.0 wt. % to 8 wt. %, from 5 wt. % to 15 wt. %, from 5 wt. % to 10 wt. %, from 5 wt. % to 8 wt. % or 6.1 wt. % electrolytes based on the total weight of the composition. In embodiments, the composition may include 4.1 wt. % potassium bicarbonate, 1.0 wt. % sodium bicarbonate, and 1.0 wt. % calcium triphosphate.

In embodiments, the composition may include a reduced concentration of sodium compared to the concentrations of other electrolytes, such as potassium, calcium, magnesium, or combinations of these. Consumption of alcoholic beverages may often be accompanied by eating and many foods consumed during consumption of alcohol can have increased amounts of sodium. Thus, sodium lost due to consumption of alcohol may often be replenished through eating foods containing sodium during alcohol consumption. The same may not be the case with other electrolytes, such as potassium, calcium, or magnesium. It has been observed that magnesium levels may be reduced in individuals Who are considered to be chronic drinkers. Calcium, potassium, and phosphates may also be lost during alcohol consumption and not replenished through the foods consumed during alcohol consumption. Thus, the composition may include a reduced amount of sodium compared to other electrolytes. In particular, the composition may include more potassium than sodium, since potassium may generally be a shortfall nutrient in many diets. In embodiments, the composition may include less than 40 mg, or less than 30 mg of sodium in a 10 gram dosage of the composition.

The composition may include one or more other additives, such as fillers or sweeteners, citric acid or citrates, colorants, flavorings, preservatives, other additives, or combinations of these. In embodiments, the composition may include one or more fillers, such as sugars, carbohydrates, or other fillers. Sugars and carbohydrates used as fillers may include but are not limited to fructose, maltodextrin, dextrose, maltose, galactose, sucrose, lactose, flour, starches, or combinations of these. Fillers may be included as a bulking agent to increase the weight and volume of a dosage or serving size of the composition, as a sweetener to alter the taste or mouth feel of the composition, as a dispersant to provide a solid powder into which active components may be distributed, or combinations of these. The presence of the fillers may promote easier preparation of solutions of water and the composition during treatment. The sugars and carbohydrates as fillers may be included in the composition to alter the taste or sweetness of the composition and/or to increase blood sugar levels to reduce or prevent headaches that may be caused by low blood sugar brought on by consumption of alcohol. Some fillers, such as maltodextrin, may be included to modify the mouth feel of a liquid mixture prepared by mixing water with the composition.

The composition may include greater than or equal to 50 wt. %, greater than or equal to 60 wt. %, or even greater than or equal to 70 wt. % fillers based on the total weight of the composition. The composition may include less than or equal to 95 wt. %, less than or equal to 90 wt. %, or even less than or equal to 80 wt. % fillers based on the total weight of the composition. In embodiments, the composition may include from 50 wt. % to 95 wt. %, from 50 wt. % to 90 wt. %, from 50 wt. % to 80 wt. %, from 60 wt. % to 95 wt. %, from 60 wt. % to 90 wt. %, from 60 wt. % to 80 wt. %, from 70 wt. % to 95 wt. %, from 70 wt. % to 90 wt. %, from 70 wt. % to 80 wt. %, or from 70 wt. % to 76 wt. % fillers based on the total weight of the composition.

In embodiments, the composition may include fructose as a filler/sweetener. The fructose may provide bulk to the composition, may increase the sweetness of the composition, and may increase blood sugar levels to reduce or prevent headaches caused by low blood sugar levels. The composition may include from 50 wt. % to 90 wt. %, from 50 wt. % to 80 wt. %, from 50 wt. % to 75 wt. %, from 60 wt. % to 90 wt. %, from 60 wt. % to 80 wt. %, from 60 wt. % to 75 wt. %, or from 65 wt. % to 70 wt. % fructose based on the total weight of the composition. In embodiments, the composition may include maltodextrin as a filler. Maltodextrin may be included to provide flavoring to the composition and to modify the mouth feel of the composition. The composition may include from 2 wt. % to 15 wt. %, from 2 wt. % to 10 wt. %, from 2 wt. % to 8 wt. %, from 5 wt. % to 15 wt. %, from 5 wt. % to 10 wt. %, or from 5 wt. % to 8 wt. % maltodextrin based on the total weight of the composition.

In embodiments, the composition may include citric acid or citrates. Citric acid or citrates may be included as a flavoring, a preservative, or both. Citric acid or citrates may also operate as a mild chelant, which may help solubilize one or more metal ingredients, such as vitamins, minerals, electrolytes, etc., when preparing a liquid mixture of the composition and water during use. Additionally, when used in combination with sodium bicarbonate, citric acid may react with the sodium bicarbonate when the composition is mixed with water during use to provide effervescence to the liquid mixture of the composition and water. The composition may include from 0.1 wt. % to 10 wt. %, from 0.1 wt. % to 5 wt. %, from 0.5 wt. % to 10 wt. %, from 0.5 wt. % to 5 wt. %, from 1 wt. % to 10 wt. %, or from 1 wt. % to 5 wt. % citric acid or citrates based on the total weight of the composition. Citrates may include magnesium citrate, trimagnesium citrate, or other metal citrates.

The composition may include one or more flavorings. The flavorings can include organic acids, such as citric acid (previously discussed), malic acid, lactic acid, or other naturally occurring organic acids. Flavorings may also include other natural or artificial sweeteners and flavorings. In embodiments, the composition may include maltodextrin as a flavoring. In embodiments, the composition may not include artificial flavorings. The composition may also include one or more natural or artificial colorants. In embodiments, the composition may include one or more fruit juices, vegetable juices, or both as colorants. In embodiments, the composition may not include natural or artificial colorants.

The composition may further include preservatives other than citric acid. The preservatives may be included in small amounts to extend the shelf life of the composition. In embodiments, the composition may not include a preservative other than citric acid.

In embodiments, the composition does not include activated carbon. Activated carbon may be present in some commercially available products for treating alcohol hangover symptoms or treating alcohol poisoning. Activated carbon is a form of carbon processed to have small, low-volume pores that increase the surface area available for adsorption or chemical reactions. However, activated carbon is useful more for treating alcohol poisoning and has not been shown to be effective for reducing or eliminating development of the detrimental effects of alcohol hangover. Additionally, activated carbon may have an adverse effect on the taste of the composition.

In embodiments, the composition does not include dihydromyricetin (DHM), which may be present in some commercially available hangover cures. DHM may act to settle the stomach; however, there is yet no direct evidence that DHM provides any other useful effect on reducing or preventing the detrimental effects of alcohol consumption. Additionally, DHM may have an adverse effect on the flavor, which is not desirable for a ready-to-drink powder formulation.

The composition may include the prickly pear extract, reduced L-Glutathione, N-Acetyl-L-Cysteine (NAC), licorice root extract, and milk thistle in effective amounts that are sufficient in combination to reduce or prevent development of one or more detrimental symptoms of alcohol consumption. In embodiments, the composition may include from 0.5 wt. % to 6 wt. % prickly pear extract, from 0.5 wt. % to 6 wt. % reduced L-Glutathione, from 0.5 wt. % to 6 wt. % N-Acetyl-L-Cysteine (NAC), from 0.5 wt. % to 6 wt. % licorice rood root extract, and from 0.2 wt. % to 6 wt. % milk thistle, wherein the weight percentages are based on the total weight of the composition. In embodiments, the composition may include from 0.001 wt. % to 0.2 wt. % biotin based on the total weight of the composition. In embodiments, the composition may further comprise one or more micronutrients. The micronutrients may include one or more vitamins, minerals, electrolytes, or combinations of these. The micronutrients may be selected from the group consisting of Vitamin C, Vitamin B6, Vitamin B12, folic acid, pantothenate, potassium, sodium, thiamine, riboflavin, selenium, zinc, or combinations of these. In embodiments, the composition may include from 0.5 wt. % to 6 wt. % vitamins and minerals based on the total weight of the composition. In embodiments, the composition may include one or more additives selected from fillers, flavorings, colorants, preservatives, or combinations of these.

In embodiments, the composition may consist or consist essentially of an active blend consisting of prickly pear extract, reduced L-Glutathione, N-Acetyl-L-Cysteine (NAC), licorice root extract, and milk thistle; optionally, one or more vitamins selected from the group consisting of Vitamin C, Vitamin E, Vitamin B-1 (thiamine), Vitamin B-2 (riboflavin), Vitamin B-3 (niacin), Vitamin B-5 (pantothenic acid), Vitamin B-6, Vitamin B-7 (biotin), Vitamin B-9 (folate), Vitamin B-12, and combinations of these; optionally, one or more minerals; optionally, one or more electrolytes; optionally, one or more fillers or sweeteners; optionally, one or more flavorings; optionally, one or more colorants; optionally, citric acid or citrates; optionally, malic acid; and, optionally, one or more preservatives. In embodiments, the composition may include the one or more vitamins selected from the group consisting of Vitamin C, Vitamin E, Vitamin B-1 (thiamine), Vitamin B-2 (riboflavin), Vitamin B-3 (niacin), Vitamin B-5 (pantothenic acid), Vitamin B-6, Vitamin B-7 (biotin), Vitamin B-9 (folate), Vitamin B-12, and combinations of these. In embodiments, the composition may include Biotin. In embodiments, the composition may include the one or more minerals. In embodiments, the one or more minerals may be selected from the group consisting of zinc, selenium, magnesium, and combinations of these. In embodiments, the composition may include the one or more electrolytes. In embodiments, the one or more electrolytes may be selected from the group consisting of sodium, potassium, chlorides, calcium, magnesium, bicarbonates, phosphates, sulfates, salts thereof, and combinations of these. In embodiments, the one or more electrolytes may include sodium bicarbonate, calcium phosphate, potassium bicarbonate, tricalcium phosphate, or combinations of these. In embodiments, the composition may include the one or more fillers or sweeteners. In embodiments, the fillers or sweeteners may be selected from the group consisting of fructose, maltodextrin, dextrose, maltose, galactose, sucrose, lactose, flour, starches, and combinations of these. In embodiments, the fillers or sweeteners may be fructose, maltodextrin, or both. In embodiments, the composition may include the citric acid or citrates. In embodiments, the composition may include the malic acid. In embodiments, the composition may include the flavorings, the colorants, or both. In embodiments, the composition may include the one or more preservatives.

The composition may be in the form of a ready-to-drink powder. The composition may also be in the form of a dissolvable tablet, a concentrated liquid, a pill, or other form. A single dosage of the composition may include a dry weight of from 5 grams to 50 grams, from 5 grams to 40 grams, from 5 grams to 30 grams, from 5 grams to 20 grams, from 5 grams to 10 grams, from 20 grams to 50 grams, from 10 grams to 40 grams, from 10 grams to 30 grams, from 10 grams to 20 grams, or about 10 grams of the composition, where the dry weight is the weight of the composition without water. The composition may be prepared and packaged by any known compounding techniques or methods known in the art of making ready-to-drink powders or tablets. Such compounding methods are well known to persons of ordinary skill in the art.

The composition may be administered to a person or consumed by a person orally to reduce or prevent the development of the detrimental effects of alcohol consumption. In embodiments, the composition may be a powder, and the composition may be administered by mixing a single dosage of the composition with water to produce a liquid mixture, which may then be consumed orally by the person. The liquid mixture may be prepared by adding a single dosage of the composition to an amount of water of from 5 fluid ounces to 8 fluid ounces (about 140 milliliters to 250 milliliters) and mixing the liquid mixture for a period of time sufficient to disperse the solid components into the water. The liquid mixture may be mixed for at least 5 seconds, at least 10 seconds, or even at least 30 seconds, such as from 5 seconds to 1 minute, or from 10 seconds to 1 minute. The composition may be administered to a person before consuming alcohol, after consuming alcohol, or both. When administered to a person before consuming alcohol, the liquid mixture can be prepared and ingested at least 1 hour or at least 30 minutes before consuming alcohol. When administered to a person after consuming alcohol, the liquid mixture should be prepared and ingested after the last amount of alcohol has been consumed. In embodiments, one dosage of the composition may be administered before consuming alcohol and a second dosage of the composition may be administered after consuming alcohol.

In embodiments, a method of reducing or preventing the development of detrimental symptoms of alcohol consumption may include ingesting a liquid mixture before or after consuming one or more alcoholic beverages, the liquid mixture comprising water and the composition that includes prickly pear extract, reduced L-Glutathione, N-Acetyl-L-Cysteine (NAC), licorice root extract, and milk thistle, which are present in amounts sufficient in combination to reduce or prevent development of one or more detrimental symptoms of alcohol consumption. The liquid mixture may be ingested orally. In embodiments, the method may include ingesting a first liquid mixture comprising a first dosage of the composition and water before ingesting one or more alcoholic beverages, and ingesting a second liquid mixture comprising a second dosage of the composition and water after ingesting the one or more alcoholic beverages, wherein the first dosage and the second dosage of the composition may reduce or prevent the development of one or more detrimental symptoms of alcohol consumption. In embodiments, the liquid mixture may include from 5 grams to 50 grams of the composition mixed into from 4 fluid ounces to 8 fluid ounces of water (140 mL to 250 mL of water), or from 4 fluid ounces to 7 fluid ounces. The composition may have any of the other constituents, compositions, or features previously described in this disclosure.

EXAMPLES

Embodiments of the present disclosure will be further clarified by the following examples. The examples are illustrative in nature, and should not be understood to limit the subject matter of the present disclosure.

The compositions according to the present disclosure was administered to a number of voluntary human participants. The composition included prickly pear extract, reduced L-Glutathione, N-Acetyl-L-Cysteine (NAC), licorice root extract, and milk thistle in concentrations within of from 0.5 wt. % to 6 wt. % for each according to the compositions disclosed herein. The compositions also included various micronutrients, such as vitamins, minerals, and electrolytes. In step 1 administration, each of the participants self-administered a first mixture comprising a 10 gram sample of the composition mixed into 8 fluid ounces of water before consuming alcoholic beverages. The participants then consumed alcoholic beverages in the quantities provided below in Table 1. At the conclusion of consuming the alcoholic beverages, each participant was instructed to self-administer a second liquid mixture comprising a 10 gram sample of the composition mixed in 8 fluid ounces of water in a step 2 administration. Each of the participants then went to sleep. The next morning, each of the participants recorded how their body felt and their observations on the effects of the composition. The observations are provided below in Table 1.

TABLE 1

| Subject | Age | Weight lbs. | Gender Identity | Alcohol consumed between step 1 and step 2 | Comments the Morning After. |
|---|---|---|---|---|---|
| 1 | 29 | 170 | M | 10 beers 4 shots of liquor | No hangover. I want more hangover cure when ready. |
| 2 | 41 | 220 | M | 2 glasses of red wine, 2 glasses of champagne and 9 rum and cokes | No hangover, fell asleep at 1:30 am woke up at 5:30 am wide awake. It took 1 hour to fall back to sleep and I woke up again at 9:30 am. I am very happy with results and want more. |
| 3 | 24 | 140 | F | 6 cocktails | I took first dose 1 hour before drinking and second dose right before bed. My typical hangover consists of a migraine headache and feeling nauseous. I woke up with neither hangover signs and felt fine. I was wide awake that morning. I want more of the hangover cure. |
| 4 | 24 | 170 | M | 12 cocktails | I took the first dose right before drinking and the second dose before going to bed. I'm usually extremely tired from drinking the night before, and I was very tired when I finally went to bed that night. But, I woke up wide awake (no hangover) with hangover cure. I want more hangover cure. |
| 5 | 36 | 190 | M | 8 whiskeys on the rocks and 4 beers | I took the formula 1 hour before drinking. I took the second dose after returning home, but then had 2 more beers. Compared to normal hangover (normal hangover is horrific) subject felt fine, but not perfect; obviously they didn't follow directions. |
| 6 | 40 | 190 | M | 8 beers 2 shots of whiskey | The participant asked if there's was niacin in formula as his face was flushed, and he typically has a bad reaction mixing alcohol and niacin. |
| 7 | 33 | 140 | F | 1 bottle of red wine | The participant asked if niacin was in formula as her faced flushed red and she felt off. She has a bad reaction when mixing alcohol and niacin. |
| 8 | 22 | 200 | M | 12 pack of 12 oz. beers | I was able to wake up refreshed and go to gym. No nausea or headache. Not yucky. |
| 9 | 25 | 160 | M | 6 12 oz. beers | I was absolutely amazed. No anxiety or drag, felt alive and full of energy. |
| 10 | 51 | 180 | M | 8 Coors lite beers and 3 shots Irish whiskey | No hangover, or typical body aches. I went for a run the following morning. |
| 11 | 35 | 150 | F | 5 glasses red wine | Wow! I did not wake up with my normal lingering half dead feeling. I felt refreshed and ready for the gym. No nausea, headache or mind anxiety. |
| 12 | 36 | 150 | F | 6 glasses red wine | My kids woke up to a happy momma! I felt great and ready for the day compared to my typical Sunday morning after my wine. |
| 13 | 35 | 140 | F | 5 glasses red wine | I just feel clean inside, refreshed. No body aches, or feeling of nausea. |
| 14 | 65 | 200 | M | 5 whiskey on the rocks | I wish I had this when I was younger. I would have been much more productive after a night out drinking. I enjoyed 18 holes of golf and felt very relaxed and calm. My stomach felt good which helped my mood too. |

TABLE 1-continued

| Subject | Age | Weight lbs. | Gender Identity | Alcohol consumed between step 1 and step 2 | Comments the Morning After. |
|---|---|---|---|---|---|
| 15 | 32 | 195 | M | 10 beers | The product not only helped me feel not hungover the next day after drinking, I felt overall much more energized than usual. Having never used a hangover prevention type of product before, it was a very surreal experience where I felt as though I should be sluggish or exhausted, my body and mind felt like they were a bit at odds at first. As the day continued on, I felt good enough to go work out at LA Fitness and maintained an impressive energy level throughout the session. I was super impressed and plan on using it again! |
| 16 | 40 | 250 | M | 22 ounces bourbon | The total alcohol consumed reflects an effort to really give the samples a good test and is far more than I would normally consume. The only water included the water with the first mixture and second mixture, the glass of water at 11:30, and the ice that melted in the drinks. Following the second dose, I slept soundly for a full 8.5 hours. The next morning, my gastrointestinal system was in good shape and I did not have a stomach ache or any other GI discomfort. The most striking effect was the noticeable absence of muscle aches and pains that I normally experience the day after consuming that much alcohol. I did not feel any lactic acid in my muscles and was able to move about as normal with little discomfort. I was tired the next morning for sure, but I did not have much of a headache and felt a whole lot better than I expected to. I was impressed by the effectiveness in preventing the hangover. |
| 17 | 45 | 210 | M | 8 beers 2 shots of tequila | I woke up feeling balanced, especially considering the amount I drank last night. |
| 18 | 44 | 240 | M | 4 vodka sodas | I felt fine in the morning, no headache, no anxiety, no nausea. These are all symptoms I can expect from a late night out. |
| 19 | 35 | 130 | F | 7 glasses red wine | My standard night-out headache was lessened and went away after late morning. I had no anxiety which is a huge positive! Can I have another packet? I felt fine by mid afternoon and proceeded to go to an event that night feeling fine. |
| 20 | 38 | 120 | F | 6 glasses red wine | I did have a dull headache and took two ibuprofen around 7. I was tired getting up, but no nausea or anxiety at all. Proceeded with daily routine and felt perfectly fine the rest of day. I was productive overall. Pleased with results. |
| 21 | 22 | 160 | M | 7 beers | Man, love this stuff! Felt great, no sluggish feeling and I was super refreshed. Ran 4 miles after wake up. Slept great too! |
| 22 | 23 | 195 | M | 10 beers | It helped bigtime. Felt like a morning when I don't drink. No ill leftover effects from drinking cheap beer. Played basketball and felt great. |
| 23 | 21 | 175 | M | 8 beers | I love the taste and how it forced me to drink water before and after. Overall my body felt good and had I a huge breakfast. |
| 24 | 26 | 180 | M | 10 beers | I feel rested and clear headed. No headache or typical hangover effects. |
| 25 | 65 | 140 | F | 4 glasses white wine | I wish I had this during my social/work happy hour functions 30 years ago. I feel wonderful this morning, no headache or GI issues. Look forward to keeping a carton of your product in my kitchen. |
| 26 | 49 | 165 | M | 5 glasses red wine | I woke up no hangover, and I'm in a really good mood. |

TABLE 1-continued

| Subject | Age | Weight lbs. | Gender Identity | Alcohol consumed between step 1 and step 2 | Comments the Morning After. |
|---|---|---|---|---|---|
| 27 | 47 | 105 | F | 2 glasses of white wine | Two glasses of white wine will make me feel ill the following morning. I felt normal this morning, no nausea or half dead feeling! |
| 28 | 32 | 150 | F | 8 vodka sodas | No fog this am. Feel . . . strangely good and clear minded. No anxiety or body discomfort. |
| 29 | 55 | 180 | M | 8 ounces of scotch | No hangover. I went to the gym and had a productive day. |
| 30 | 35 | 200 | F | 8 beers | No hangover. I had much more energy than normal. |
| 31 | 37 | 140 | F | 5 margaritas | Finally, something that's easy to take . . . and taste great too. I feel great today, no standard negative effects. |
| 32 | 35 | 130 | F | 5 glasses white wine | No headache or nausea. Also, I don't feel the usual overall yuck feeling. |
| 33 | 40 | 130 | F | 4 glasses white wine | I'm impressed. I feel pretty good, no GI discomfort or feelings of anxiety. |
| 34 | 22 | 180 | M | 10 beers | I felt and still feel great. I played golf this am and had a clear head. |
| 35 | 24 | 220 | M | 12 beers | Love this stuff. I feel great today, and heading to gym now, no hangover. |
| 36 | 40 | 200 | M | 2 glasses of red wine and 5 vodka sodas | I could have used this during my Army days, especially in preparation for morning runs. I feel great, no hangover. |
| 37 | 37 | 150 | F | 4 glasses white wine | I feel good, fine . . . better than normal. My mind is clear, and no body aches. |

Overall, the greatest majority of the participants experienced a noticeable and sometimes remarkable reduction in the development of their typical symptoms of alcohol consumption. Participants 6 and 7 experienced interactions between alcohol and niacin in the composition. Thus, it was found that niacin should not be included in the compositions of the present disclosure. Participant number 5 did not follow the proper instructions for use by continuing to consume alcohol after administering the second step dosage. As a result, participant 5 reported less of an effect, but still observed a reduction in the severity of the hangover symptoms.

A first aspect of the present disclosure is directed to a composition for reducing or preventing development of one or more symptoms of alcohol consumption. The composition may include prickly pear extract, reduced L-Glutathione, N-Acetyl-L-Cysteine (NAC), licorice root extract, and milk thistle.

A second aspect of the present disclosure may include the first aspect, wherein the prickly pear extract, reduced L-Glutathione, N-Acetyl-L-Cysteine (NAC), licorice root extract, and milk thistle may be present in the composition in effective amounts that may be sufficient in combination to reduce or prevent development of one or more detrimental symptoms of alcohol consumption.

A third aspect of the present disclosure may include either one of the first or second aspects, comprising from 0.5 wt. % to 6 wt. % prickly pear extract based on the total weight of the composition.

A fourth aspect of the present disclosure may include any one of the first through third aspects, comprising from 0.5 wt. % to 6 wt. % reduced L-Glutathione based on the total weight of the composition.

A fifth aspect of the present disclosure may include any one of the first through fourth aspects, comprising from 0.5 wt. % to 6 wt. % NAC based on the total weight of the composition.

A sixth aspect of the present disclosure may include any one of the first through fifth aspects, comprising from 0.5 wt. % to 6 wt. % licorice rood extract based on the total weight of the composition.

A seventh aspect of the present disclosure may include any one of the first through sixth aspects, comprising from 0.2 wt. % to 6 wt. % milk thistle based on the total weight of the composition.

An eighth aspect of the present disclosure may include any one of the first through seventh aspects, wherein the milk thistle may comprise a milk thistle extract comprising greater than or equal to 80 wt. % silymarin based on the total weight of the milk thistle extract.

A ninth aspect of the present disclosure may include any one of the first through eighth aspects, comprising from 0.5 wt. % to 6 wt. % prickly pear extract, from 0.5 wt. % to 6 wt. % reduced L-Glutathione, from 0.5 wt. % to 6 wt. % N-Acetyl-L-Cysteine (NAC), from 0.5 wt. % to 6 wt. % licorice root extract, and from 0.2 wt. % to 6 wt. % milk thistle, wherein the weight percentages are based on the total weight of the composition.

A tenth aspect of the present disclosure may include any one of the first through ninth aspects, further comprising biotin.

An eleventh aspect of the present disclosure may include the tenth aspect, comprising from 0.001 wt. % to 0.2 wt. % biotin based on the total weight of the composition.

A twelfth aspect of the present disclosure may include any one of the first through eleventh aspects, further comprising one or more micronutrients.

A thirteenth aspect of the present disclosure may include the twelfth aspect, wherein the micronutrients comprise one or more vitamins, minerals, electrolytes, or combinations of these.

A fourteenth aspect of the present disclosure may include either one of the twelfth or thirteenth aspects, wherein the micronutrients are selected from the group consisting of vitamin C, vitamin B6, vitamin B12, folic acid, pantothenate, potassium, sodium, thiamine, riboflavin, selenium, zinc, or combinations of these.

A fifteenth aspect of the present disclosure may include any one of the first through fourteenth aspects, comprising from 0.5 wt. % to 6 wt. % vitamins and minerals based on the total weight of the composition.

A sixteenth aspect of the present disclosure may include any one of the first through fifteenth aspects, further comprising one or more additives selected from fillers, flavorings, colorants, preservatives, or combinations of these.

A seventeenth aspect of the present disclosure may include any one of the first through sixteenth aspects, wherein the composition comprises a powder or a tablet.

An eighteenth aspect of the present disclosure may include any one of the first through seventeenth aspects, wherein the composition does not include activated charcoal.

A nineteenth aspect of the present disclosure may include any one of the first through eighteenth aspects, wherein the composition does not include dihydromyricetin.

A twentieth aspect of the present disclosure may include any one of the first through nineteenth aspects, wherein the composition does not include niacin (Vitamin B-3).

A twenty-first aspect of the present disclosure may be directed to methods of preventing or reducing the development of one or more detrimental symptoms of alcohol consumption. The methods may include ingesting a liquid mixture before or after consuming one or more alcoholic beverages. The liquid mixture may comprise water and a composition that includes effective amounts of each of prickly pear extract, reduced L-Glutathione, N-Acetyl-L-Cysteine (NAC), licorice root extract, and milk thistle in order to reduce or prevent development of one or more symptoms of alcohol consumption.

A twenty-second aspect of the present disclosure may include the twenty-first aspect, comprising ingesting a first liquid mixture comprising a first dosage of the composition and water before ingesting one or more alcoholic beverages and ingesting a second liquid mixture comprising a second dosage of the composition and water after ingesting the one or more alcoholic beverages, wherein the first dosage and the second dosage may reduce or prevent the development of symptoms of alcohol consumption.

A twenty-third aspect of the present disclosure may include either one of the twenty-first or twenty-second aspects, wherein the liquid mixture may comprise from 5 grams to 50 grams of the composition mixed into from 4 fluid ounces to 8 fluid ounces of water, or from 4 fluid ounces to 7 fluid ounces of water.

A twenty-fourth aspect of the present disclosure may include any one of the twenty-first through twenty-third aspects, further comprising preparing the liquid mixture by combining a single dosage of the composition with from 4 fluid ounces to 8 fluid ounces of water to produce the liquid mixture and mixing the liquid mixture for a period of time sufficient to disperse the solid materials in the water.

A twenty-fifth aspect of the present disclosure may include any one of the twenty-first through twenty-fourth aspects, wherein the composition may comprise from 0.5 wt. % to 6 wt. % prickly pear extract based on the total weight of the composition.

A twenty-sixth aspect of the present disclosure may include any one of the twenty-first through twenty-fifth aspects, wherein the composition may comprise from 0.5 wt. % to 6 wt. % reduced L-Glutathione based on the total weight of the composition.

A twenty-seventh aspect of the present disclosure may include any one of the twenty-first through twenty-sixth aspects, wherein the composition may comprise from 0.5 wt. % to 6 wt. % NAC based on the total weight of the composition.

A twenty-eighth aspect of the present disclosure may include any one of the twenty-first through twenty-seventh aspects, wherein the composition may comprise from 0.5 wt. % to 6 wt. % licorice rood extract based on the total weight of the composition.

A twenty-ninth aspect of the present disclosure may include any one of the twenty-first through twenty-eighth aspects, wherein the composition may comprise from 0.2 wt. % to 6 wt. % milk thistle based on the total weight of the composition.

A thirtieth aspect of the present disclosure may include any one of the twenty-first through twenty-ninth aspects, wherein the milk thistle may be a milk thistle extract comprising greater than or equal to 80% silymarin based on the total weight of the milk thistle extract.

A thirty-first aspect of the present disclosure may include any one of the twenty-first through thirtieth aspects, wherein the composition may comprise from 0.5 wt. % to 6 wt. % prickly pear extract, from 0.5 wt. % to 6 wt. % reduced L-Glutathione, from 0.5 wt. % to 6 wt. % N-Acetyl-L-Cysteine (NAC), from 0.5 wt. % to 6 wt. % licorice root extract, and from 0.2 wt. % to 6 wt. % milk thistle, wherein the weight percentages are based on the total weight of the composition.

A thirty-second aspect of the present disclosure may include any one of the twenty-first through thirty-first aspects, wherein the composition may comprise biotin.

A thirty-third aspect of the present disclosure may include the thirty-second aspect, wherein the composition may comprise from 0.001 wt. % to 0.2 wt. % biotin based on the total weight of the composition.

A thirty-fourth aspect of the present disclosure may include any one of the twenty-first through thirty-third aspects, wherein the composition may comprise one or more micronutrients.

A thirty-fifth aspect of the present disclosure may include the thirty-fourth aspect, wherein the micronutrients may comprise one or more vitamins, minerals, electrolytes, or combinations of these.

A thirty-sixth aspect of the present disclosure may include either one of the thirty-fourth or thirty-fifth aspects, wherein the micronutrients may be selected from the group consisting of vitamin C, vitamin B6, vitamin B12, folic acid, pantothenate, potassium, sodium, thiamine, riboflavin, selenium, zinc, or combinations of these.

A thirty-seventh aspect of the present disclosure may include any one of the twenty-first through thirty-sixth aspects, wherein the composition may comprise from 0.5 wt. % to 6 wt. % vitamins and minerals based on the total weight of the composition.

A thirty-eighth aspect of the present disclosure may include any one of the twenty-first through thirty-seventh aspects, wherein the composition may comprise one or more additives selected from fillers, flavorings, colorants, preservatives, or combinations of these.

A thirty-ninth aspect of the present disclosure may include any one of the twenty-first through thirty-eighth aspects, wherein the composition may be a powder or a tablet.

A fortieth aspect of the present disclosure may include any one of the twenty-first through thirty-ninth aspects, wherein the composition does not include activated charcoal.

A forty-first aspect of the present disclosure may include any one of the twenty-first through fortieth aspects, wherein the composition does not include dihydromyricetin.

A forty-second aspect of the present disclosure may include any one of the twenty-first through forty-first aspects, wherein the composition does not include niacin (Vitamin B-3).

It should be understood that any two quantitative values assigned to a property or composition may constitute a range of that property or composition, and all combinations of ranges formed from all stated quantitative values of a given property or composition are contemplated in this disclosure. It should be appreciated that compositional ranges of a constituent in a composition or formulation should be appreciated as containing, in some embodiments, a mixture of isomers of that constituent. It should be appreciated that the examples supply compositional ranges for various compositions, and that the total amount of isomers of a particular chemical composition can constitute a range.

Further, it should be apparent to those skilled in the art that various modifications and variations can be made to the described embodiments without departing from the spirit and scope of the claimed subject matter. Thus, it is intended that the specification cover the modifications and variations of the various described embodiments provided such modification and variations come within the scope of the appended claims and their equivalents.

What is claimed is:

1. A composition for reducing development of one or more symptoms of alcohol consumption, the composition comprising:
   from 0.5 wt. % to 3 wt. % prickly pear extract,
   from 0.5 wt. % to 3 wt. % reduced L-Glutathione,
   from 0.5 wt. % to 3 wt. % N-Acetyl-L-Cysteine (NAC),
   from 0.5 wt. % to 3 wt. % licorice root extract, and
   from 0.2 wt. % to 3 wt. % milk thistle, wherein the weight percentages are based on the total weight of the composition;
   wherein the composition does not include dihydromyricetin.

2. The composition of claim 1, wherein the milk thistle comprises a milk thistle extract comprising greater than or equal to 80 wt. % silymarin based on the total weight of the milk thistle extract.

3. The composition of claim 1, comprising from 0.001 wt. % to 0.2 wt. % biotin based on the total weight of the composition.

4. The composition of claim 1, further comprising one or more micronutrients comprising one or more vitamins, minerals, electrolytes, or combinations of these.

5. The composition of claim 4, wherein the micronutrients are selected from the group consisting of vitamin C, vitamin B6, vitamin B12, folic acid, pantothenate, potassium, sodium, thiamine, riboflavin, selenium, zinc, or combinations of these.

6. The composition of claim 1, wherein the composition is in the form of a powder or a tablet.

7. A method of preventing or reducing the development of one or more detrimental symptoms of alcohol consumption, the method comprising:
   ingesting a liquid mixture before or after consuming one or more alcoholic beverages, the liquid mixture comprising water and the composition of claim 1, in order to reduce or prevent development of one or more symptoms of alcohol consumption.

8. The method of claim 7, comprising:
   ingesting a first liquid mixture comprising a first dosage of the composition and water before ingesting one or more alcoholic beverages; and
   ingesting a second liquid mixture comprising a second dosage of the composition and water after ingesting the one or more alcoholic beverages, wherein the first dosage and the second dosage reduce or prevent the development of symptoms of alcohol consumption.

9. The method of claim 7, wherein the liquid mixture comprises from 5 grams to 50 grams of the composition mixed into from 4 fluid ounces to 8 fluid ounces of water.

10. The method of claim 7, further comprising preparing the liquid mixture by combining a single dosage of the composition with from 5 fluid ounces to 8 fluid ounces of water to produce the liquid mixture and mixing the liquid mixture for a period of time sufficient to disperse the solid materials in the water.

11. The method of claim 7, wherein the composition comprises from 0.001 wt. % to 0.2 wt. % biotin based on the total weight of the composition.

12. The method of 7, wherein the composition comprises one or more micronutrients selected from the group consisting of vitamin C, vitamin B6, vitamin B12, folic acid, pantothenate, potassium, sodium, thiamine, riboflavin, selenium, zinc, or combinations of these.

13. The method of claim 7, wherein the composition comprises a powder or a tablet.

14. The composition of claim 1, wherein the composition does not include activated charcoal.

15. The composition of claim 1, further comprising zinc, selenium, or both.

16. The composition of claim 15, comprising from 0.01 wt. % to 0.10 wt. % zinc based on the total weight of the composition.

17. The composition of claim 15, comprising from 1 microgram to 50 micrograms selenium in a 10 gram dosage amount of the composition.

18. A composition for reducing development of one or more symptoms of alcohol consumption, the composition consisting of:
   from 0.5 wt. % to 6 wt. % prickly pear extract based on the total weight of the composition;
   from 0.5 wt. % to 6 wt. % reduced L-Glutathione based on the total weight of the composition;
   from 0.5 wt. % to 6 wt. % N-Acetyl-L-Cysteine (NAC) based on the total weight of the composition;
   from 0.5 wt. % to 6 wt. % licorice root extract based on the total weight of the composition; and
   from 0.2 wt. % to 6 wt. % milk thistle based on the total weight of the composition;
   optionally, one or more vitamins selected from the group consisting of vitamin C, vitamin E, vitamin B-1, vitamin B-2, vitamin B-5, vitamin B-6, vitamin B-7, vitamin B-9, vitamin B-12, and combinations thereof;
   optionally, one or more minerals selected from the group consisting of zinc, selenium, magnesium, and combinations thereof;
   optionally, one or more electrolytes selected from the group consisting of calcium, sodium, potassium, bicarbonates, phosphate, and combinations of these;
   optionally, one or more fillers selected from the group consisting of fructose, maltodextrin, dextrose, maltose, galactose, sucrose, lactose, flour, starches, and combinations of these; and optionally, one or more additives selected from the group consisting of citric acid, citrates, flavorings, colorants, preservatives, and combinations of these.

\* \* \* \* \*